United States Patent [19]
Smits

[11] Patent Number: 5,344,429
[45] Date of Patent: Sep. 6, 1994

[54] PULSE ROUTING APPARATUS FOR CARDIOVERSION AND DEFIBRILLATION

[75] Inventor: Karel F. A. A. Smits, Oirsheck, Netherlands

[73] Assignee: Medtronic, Inc., Minneapolis, Minn.

[21] Appl. No.: 110,041

[22] Filed: Aug. 20, 1993

[51] Int. Cl.⁵ .............................................. A61N 1/39
[52] U.S. Cl. ......................................................... 607/5
[58] Field of Search ...................... 607/5, 4, 68, 70, 74

[56] References Cited

U.S. PATENT DOCUMENTS

| | | |
|---|---|---|
| 3,605,754 | 9/1971 | Jaros . |
| 4,641,656 | 2/1987 | Smits . |
| 4,708,145 | 11/1987 | Tacker, Jr. . |
| 4,727,877 | 3/1988 | Kallok . |
| 4,800,883 | 1/1989 | Winstrom . |
| 4,850,357 | 7/1989 | Bach, Jr. . |
| 4,953,551 | 9/1990 | Mehra . |
| 4,998,531 | 3/1991 | Bocchi et al. ............................ 607/5 |
| 5,163,427 | 11/1992 | Keimel . |

Primary Examiner—William E. Kamm
Assistant Examiner—Kennedy J. Schaetzle
Attorney, Agent, or Firm—Reed A. Duthler; Harold B. Patton

[57] ABSTRACT

A pulse routing circuit for use in conjunction with a multiple channel defibrillator. The circuit, when coupled to a multiple channel defibrillator allows for the selection of a wide variety of multiple electrode pulse regimens and waveforms, accomplished by selective interconnection of defibrillation electrodes to the pulse routing circuit. Because the circuit employs passive switching elements, such as diodes, complex switching circuitry is not required.

11 Claims, 4 Drawing Sheets

PULSE ROUTING APPARATUS FOR CARDIOVERSION AND DEFIBRILLATION

BACKGROUND OF THE INVENTION

This invention relates generally to the field of electrical stimulators, and more particularly to cardioverters and defibrillators.

The earliest cardioverters and defibrillators generated either a single burst of alternating current or a single pulse for application to the heart to cause cardioversion or defibrillation. However, the use of multiple pulses to accomplish cardioversion or defibrillation has also been extensively researched. For example, U.S. Pat. No. 3,605,754 issued to Jaros, et al., on Sep. 20, 1971 discloses an early double pulse heart defibrillator employing two capacitors which are successively discharged between a single pair of electrodes. Later, the use of multiple electrode systems, in which defibrillation pulses were delivered successively between different electrode pairs chosen from among the electrodes available was suggested. For example, U.S. Pat. No. 4,727,877 issued to Kallok on Mar. 1, 1988 and U.S. Pat. No. 4,708,145 issued to Tacker, Jr. et al., on Nov. 24, 1987, both disclose a variety of implantable, multiple electrode systems adapted for use in conjunction with a sequential pulse defibrillator, in which pulses are applied sequentially to different pairs of electrodes.

More recently, delivery of pulses simultaneously between multiple electrode pairs has been extensively pursued. For example, U.S. Pat. No. 4,953,551, issued to Mehra et al., on Sep. 4, 1990, discloses simultaneous delivery of pulses between the superior vena cava and the right ventricle and between the right ventricle and a subcutaneous electrode.

The ability to deliver sequential and simultaneous pulses to different pairs of electrodes is incorporated in the Mealtronic implantable pacemaker/cardioverter/-defibrillators presently in commercial distribution in the United States. Pulse generation circuitry for delivering such pulses is disclosed in U.S. Pat. No. 5,163,427 issued to Keimel. In the Keimel patent, two capacitor banks are provided which are simultaneously charged and then successively or simultaneously discharged between different pairs of electrodes.

It has also been proposed to apply biphasic pulses to individual electrode pairs, in which a positive pulse is followed by a negative pulse, typically having an initial amplitude equal to the trailing edge amplitude of the first pulse, but at a reversed polarity. Apparatus for delivering such biphasic pulses are disclosed in U.S. Pat. No. 4,850,357 issued to Bach, Jr. on Jul. 25, 1989, U.S. Pat. No. 4,953,551 issued to Mehra et al., on Sep. 4, 1990, and in U.S. Pat. No. 4,800,883 issued Jan. 31, 1989 to Winstrom. In all three references, it is proposed to deliver the biphasic pulse by the use of a single capacitor or a capacitor bank in which capacitors are charged and discharged together to deliver the biphasic pulse.

An alternative multiple pulse, multiple electrode defibrillation pulse regimen, referred to as the "peripheral rotating pulse" regimen, is disclosed in U.S. Pat. No. 4,641,656, issued to Stairs. This patent proposes delivery of sequential pulses, each of which employs a set of three or more electrodes, with the relative polarities of one or more electrode pairs reversed between pulses. This pulse regimen provides the ability to alter the defibrillation pulse vector between pulses, without leaving one or more electrodes inactive during individual pulses. In addition, at those electrodes which have their polarities reversed, a biphasic waveform is effectively provided.

SUMMARY OF THE INVENTION

The present invention provides a simplified routing circuit for sequentially applying pulses to multiple electrodes, including pulses delivered according to the peripheral rotating pulse regimen described in the above-cited Smits patent. The present invention is also useful in practicing variants to the peripheral rotating pulse regimen as described above, in which the polarity of only one electrode within the electrode set may change between pulses.

The present invention is adapted to be used in the context of a defibrillator having at least two separate output channels, and capable of sequentially delivering defibrillation or cardioversion pulses on each of the output channels. The present invention includes pulse routing circuitry, including a steering network, coupled to the output channels of the defibrillator and to three or more electrodes, arranged in or around the heart. The output channels of the defibrillator, the steering network and the electrodes are interconnected in a fashion such that during delivery of a first pulse, the electrodes are coupled by the steering network to the first and second output channels such that during generation of the output pulse on the first channel, the electrodes are connected to provide a first set of polarities and such that during generation of the output pulse on the second channel, the electrodes are connected to provide a second set of polarities, different from the first set of polarities.

The steering network employs passive switching elements rendered conductive by signals of proper polarity at their inputs. In the disclosed embodiments the switching elements take the form of unidirectionally conductive elements, such as diodes. The steering network provides for variation of the defibrillation or cardioversion vector between the sequentially applied pulses, without the necessity of complicated high voltage switching and switch control circuitry typically employed. The diodes within the steering matrix are individually rendered conductive or nonconductive by delivery of defibrillation pulses of proper polarities on the output channels, and require no independent timing or control circuitry to accomplish the desired polarity switching between sequentially applied pulses.

In its illustrated embodiment, the diode matrix is adapted to be coupled to the output channels of a two channel defibrillator, and provides for interconnection with two to four electrodes. However, the invention could readily be expanded to accept outputs from three or more defibrillation channels, to be sequentially applied to a larger number of electrodes. Similarly, while the embodiment as illustrated allowed for interconnection of four electrodes, additional electrodes may also be connected, typically common with one or more other electrode. Alternatively, the diode matrix may be connected to fewer than four electrodes. For example, the peripheral rotating pulse regimen and variants thereof may be practiced with three electrodes. If only two electrodes are employed, the diode matrix may be employed to allow delivery of dual monophasic pulses. As such, the present invention provides an extremely flexible yet simple mechanism for controlling the polarities of electrodes during sequentially applied pulses, delivered to two or more electrodes.

DETAILED DESCRIPTION OF THE DRAWINGS

Figure 1:
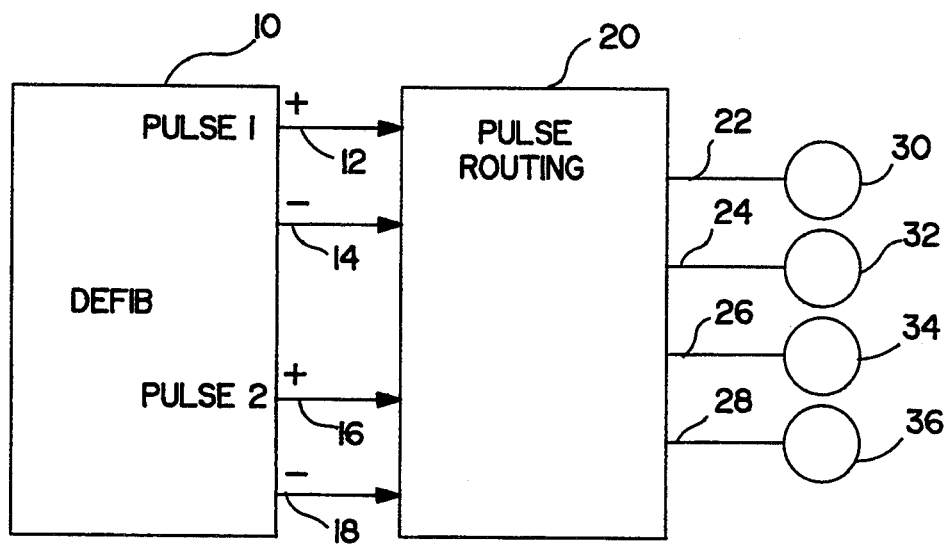
FIG. 1 is a block diagram of a pulse routing circuit according to the present invention coupled to a prior art two channel defibrillator, to provide an apparatus which may be employed to deliver the peripheral rotating pulse regimen.

FIG. 1 is a block diagram of an apparatus according to the present invention. The illustrated two channel defibrillator 10 may correspond, for example, to the Medtronic Model 2394 External Cardioverter/Defibrillator. This device, available commercially for animal use only, includes two output channels, including channel 1, illustrated schematically by output lines 12 and 14 and channel 2, illustrated schematically by output lines 16 and 18. Pulses may be delivered sequentially on the two channels (one pulse per channel), at either polarity, with tilt, amplitude and duration independently controllable for each channel. However, for purposes of understanding the present invention, output lines 12 and 16 should be presumed to always be positive and output lines 14 and 18 should be presumed to always be negative during pulse delivery. It should also be understood that the output lines associated with each output channel are disconnected from the circuitry within the defibrillator except during delivery of a pulse, and that pulses are delivered sequentially with no overlap. The output circuitry of the Medtronic Model 2394 External Cardioverter/Defibrillator corresponds to the output circuitry of an implantable defibrillator, but is packaged in a form appropriate for use in research functions. However, the present invention is just as readily practiced in conjunction with similar output circuitry, embodied in the form of an implantable device. The pulse routing circuitry 20 receives the outputs from channel I and channel 2 of the defibrillator, and selectively couples lines 12, 14, 16 and 18 to lines 22, 24, 26 and 28, which are in turn coupled to electrodes 30, 32, 34 and 36, respectively.

Figure 2:
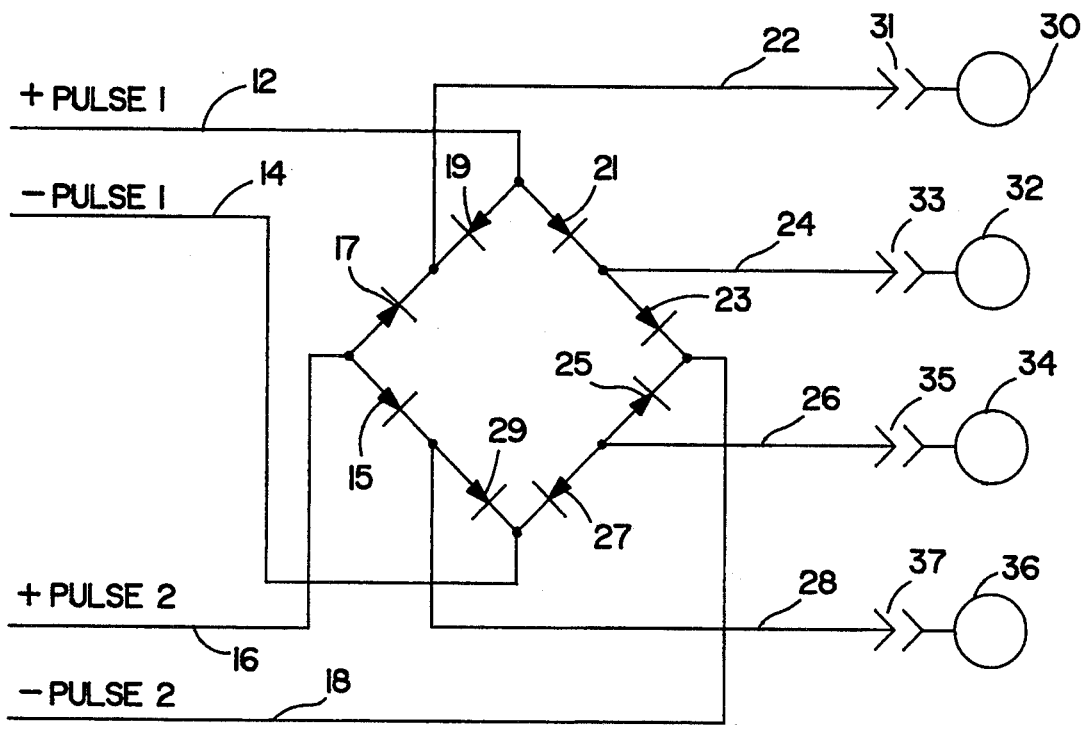
FIG. 2 is a schematic diagram of the steering network within the pulse routing circuitry.

FIG. 2 illustrates the diode steering matrix within the pulse routing circuitry 10, and its interconnection to the input lines 12, 14, 16 and 18 and the output lines 22, 24, 26 and 28, all corresponding to identically labeled structure in FIG. 1. Electrodes 30, 32, 34 and 36 are coupled to output lines 22, 24, 26 and 28, respectively, by means of electrical connectors illustrated schematically at 31, 33, 35 and 37, respectively. As illustrated, during delivery of a cardioversion or defibrillation pulse on channel 1, electrodes 30 and 32 are actively coupled to pulse 1+ line 12 by diodes 19 and 21, while electrodes 34 and 36 are actively coupled to pulse 1− line 14 by diodes 29 and 27. Similarly, during delivery of a cardioversion or defibrillation pulse on channel 2, pulse 2+ line 16 is actively coupled to electrodes 30 and 36 by diodes 17 and 15, while pulse 2− line 18 is actively coupled to electrodes 32 and 34 by diodes 23 and 25. Channel 1 and channel 2 may be activated in either order. Connectors 31, 33, 35 and 37 allow any electrode to be Coupled to any connector, further adding to the flexibility of the system.

Alternatively, only 3 of the electrodes may be employed. This will not interfere with the operation of the device to provide a multiple pulse, multiple electrode pulse regimen. For example, if electrode 30 is omitted, then during delivery of a pulse on channel 1, electrode 32 will be positive, with electrodes 34 and 36 negative. During delivery of a pulse on the pulse 2 channel, electrode 36 will be positive, with electrodes 32 and 34 negative. If electrode 32 is omitted, during application of a defibrillation pulse on the pulse 1 channel, electrode 30 is positive with electrodes 34 and 36 negative, while during delivery of a pulse on the pulse 2 channel, electrodes 30 and 36 are positive, with electrode 34 negative. If electrode 34 is omitted, during delivery of a defibrillation or cardioversion pulse on the pulse 1 channel, electrodes 30 and 32 will be positive and electrode 36 negative. During delivery of a cardioversion pulse on the pulse 2 channel, electrodes and 30 and 36 will be positive with electrode 32 negative. If electrode 36 is omitted, during delivery of a pulse on the pulse 1 channel, electrodes 30 and 32 will be positive with electrode 34 negative during delivery of a pulse on the pulse 2 channel, electrode 30 will be positive with electrodes 32 and 34 negative.

As such, by selectively coupling three electrodes to the pulse routing circuitry, a wide variety of alternative multiple pulse regimens may readily be obtained, providing great flexibility, without the necessity of complicated or extensive switching circuitry. In the context of an implantable device, a three electrode system may readily be accomplished simply by choosing which of four available output ports, corresponding to connectors 31, 33, 35 and 37 on an implantable defibrillator are to be employed, with the unused port being sealed with a plug or by means of medical adhesive. Similarly, by choosing which of the electrodes are coupled to which output port, a wide variety of spatial orientations for the pulse regimens can be accomplished. For example, a defibrillation electrode system may include electrodes located in the right ventricle, right atrium/superior vena cava, coronary sinus, and/or subcutaneous electrodes. Depending upon the specific electrode coupled to the specific output port of the defibrillator, and depending upon the number of electrodes selected, a wide variety of spatial configurations and pulse delivery regimens may be readily accomplished with almost no additional complexity added to the implantable defibrillator. Examples of the types of electrode configurations that may be obtained, in the context of an implantable defibrillator are set forth below in conjunction with the descriptions of FIGS. 4, 5, 6, 7, 8, 9 and 10.

The disclosed invention may also usefully be employed using only two electrodes. Even if the if the defibrillator to which the matrix is coupled does not have the capability to produce biphasic pulses or pulses of both polarities, the diode matrix may be employed to do so. For example, if electrodes 30 and 34 are omitted, during delivery of a pulse on the pulse 1 channel, electrode 32 will be positive and electrode 36 will be negative, During delivery of a subsequent pulse on the pulse 2 channel, electrode 36 will be positive and electrode 32 will be negative, thus providing a biphasic waveform. If the pulse amplitudes and durations of the two channels of the defibrillator are independently controllable, a wide variety of biphasic waveforms may be produced.

Figure 3:
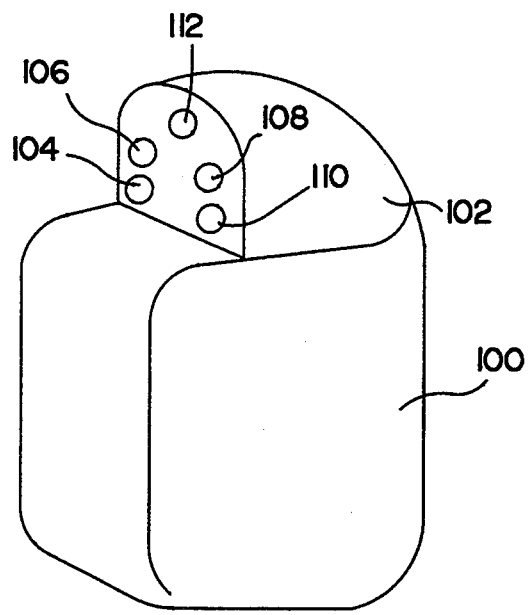
FIG. 3 is a plan drawing of an implantable defibrillator in which the invention may be practiced.

FIG. 3 illustrates an implantable defibrillator 100, which includes the circuitry of FIG. 2, in conjunction with cardioversion output circuitry corresponding generally to the output circuitry of the defibrillator 10, illustrated inn FIG. 1 and correspondingly connected thereto. The defibrillator 100 is provided with a connector assembly 102, provided with connector ports 104, 106, 108 and I 10, each of which includes an electrical connector of the type typically used in implantable defibrillators, coupled to the circuitry of FIG. 2 in a fashion corresponding to connectors 23, 25, 27 and 29 in FIG. 2. A fifth connector port I 12 is illustrated for use in coupling the defibrillator to cardiac pacing and sensing electrodes. In use, each defibrillation electrode will be provided with a corresponding connector plug, insertable in any of connector bores 104, 106, 108 and 110.

Figure 4:
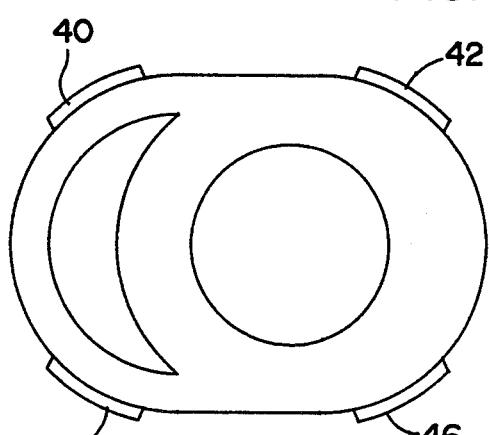
FIGS. 4, 5, 6 and 7 are simulated cross sectional views through a human heart, illustrating schematically a variety of electrode locations which may be employed in conjunction with the circuitry of FIGS. 1 and 2, to provide a variety of multiple pulse, multiple electrode pulse regimens.

FIG. 4 illustrates an electrode system employing four strip electrodes, arranged around the ventricles of the human heart. These electrodes may correspond to the electrodes illustrated in U.S. Pat. No. 4,548,203 issued to Tacker et al and incorporated herein by reference in its entirety, or to other epicardial electrodes. Included are a right posterior electrode 40 (RP) a left posterior electrode 42 (LP) a left anterior electrode 46 (LA) and a right anterior electrode 44 (RA). By selectively interconnecting these four electrodes with the pulse routing circuitry of FIG. 2, a wide variety of pulse regimens may be obtained. In the context of an implantable device, selective interconnection would be accomplished simply by choosing to which connector port each electrode is coupled.

Figure 5:
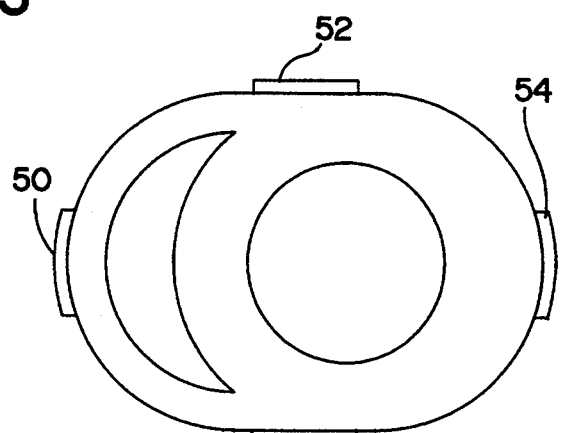

FIG. 5 illustrates a simulated cross-section through a human heart, illustrating an alternative arrangement of four electrodes, arranged around the ventricles. The electrodes include a posterior septal electrode 52 (PS) a ventricular electrode 54 (LV), an anterior septal electrode 56 (AS) and a right ventricular electrode 50 (RV).

Figure 6:
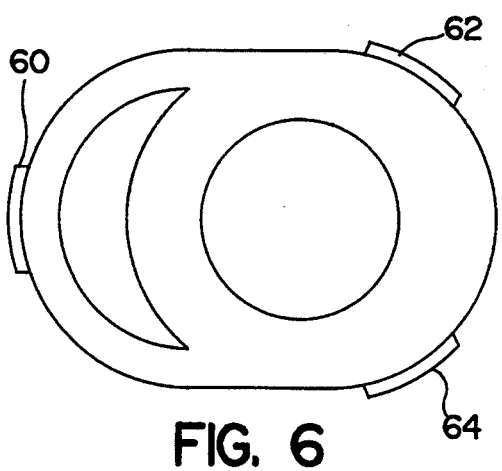

FIG. 6 illustrates a simulated cross-section through the ventricles of the human heart, illustrating a three electrode system including a right ventricle electrode 60 (RV), a left posterior electrode 62 (LP) and a left anterior electrode 64 (LA). These electrodes may similarly be selectively interconnected to the steering circuitry of FIG. 2 to provide a wide variety of pulse regimens. In the context of the implantable device illustrated in FIG. 3, selective interconnection would include selecting which connector ports are employed, as well as selecting which electrodes are coupled to the ports employed.

Figure 7:
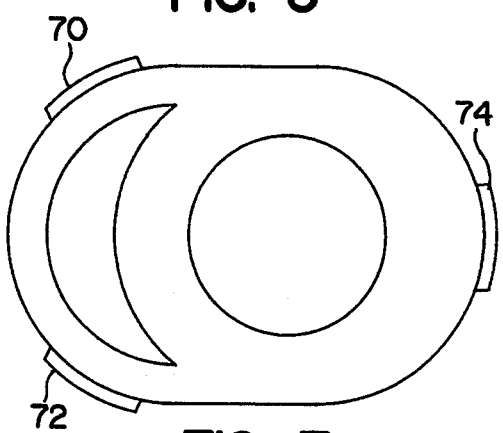

FIG. 7 illustrates a simulated cross-section through the ventricles of the human heart, illustrating an alternative three electrode configuration including a left ventricular electrode 74 (LV), a right anterior electrode 72 (RA) and a right posterior electrode 70 (RP).

Figure 8:
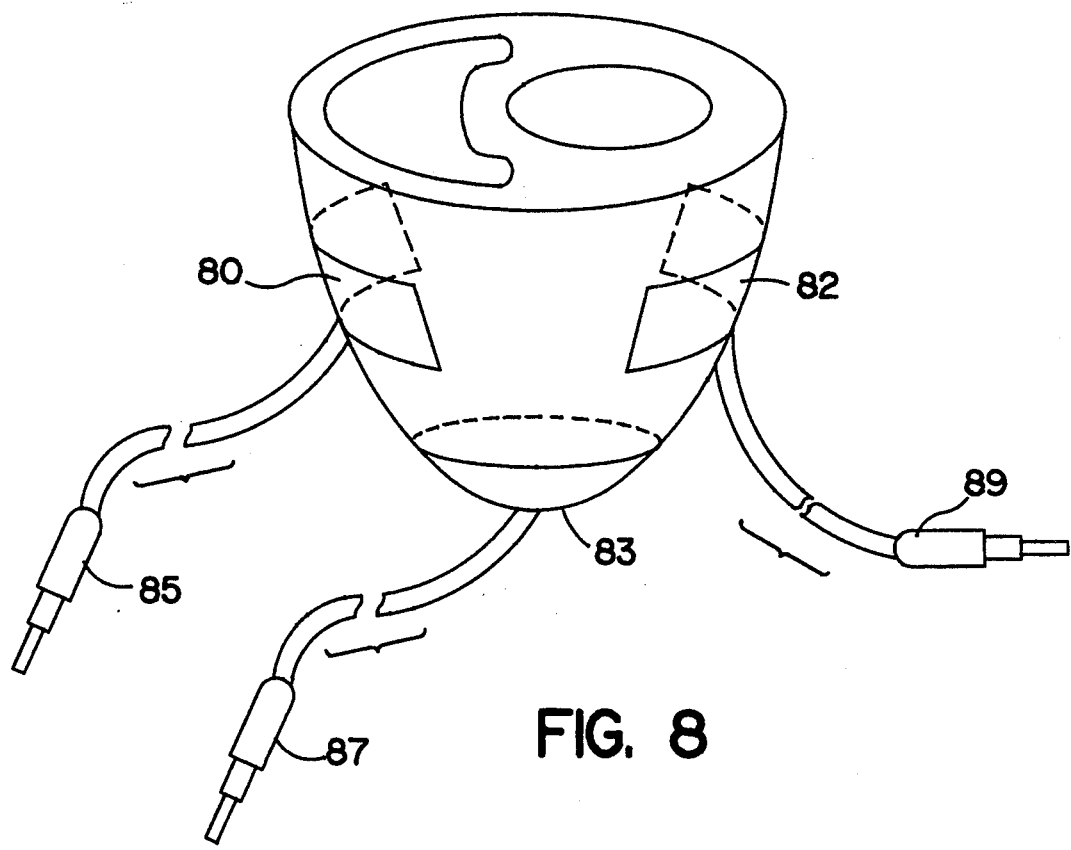
FIGS. 8 and 9 are simulated cutaway views of the ventricles of the human heart, illustrating additional alternative electrode configurations which may be employed in conjunction with the circuitry of FIGS. 1 and 2.

FIG. 8 illustrates a cutaway view of the ventricles of a human heart, along with a third alternative three electrode system, including a right ventricular electrode 80 (RV), a left ventricular electrode 82 (LV) and an apical electrode 83. In this figure, the connector plugs 85, 87 and 89, coupled to electrodes 80, 83 and 82 respectively, as referred to in the discussion of FIG. 3 are also illustrated. The illustrated electrodes, may be selectively interconnected with the pulse steering circuitry of FIG. 2 in the same fashion as discussed in conjunction with FIG. 6.

Figure 9:
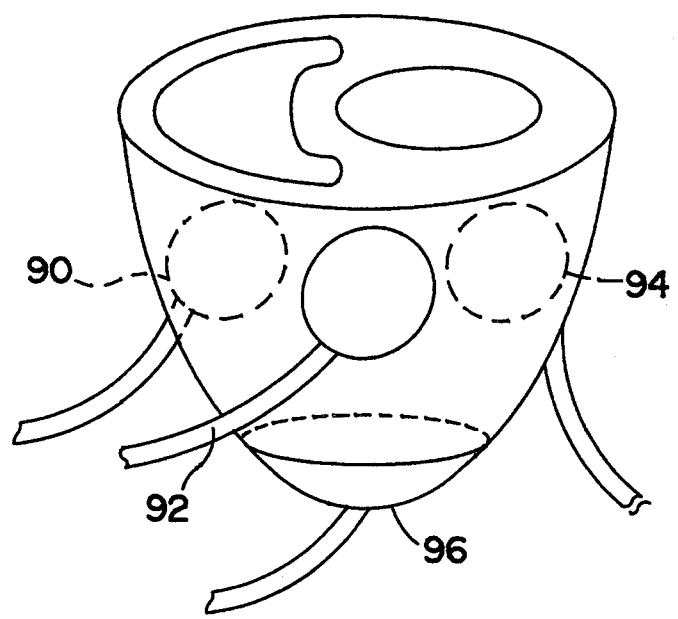

FIG. 9 illustrates a cutaway view of the ventricles of a human heart, illustrating a third alternative four electrode system, including a right posterior electrode 90 (RP), an anterior septal electrode 92 (AS), a left posterior electrode 94 (LP) and apex electrode 96 (A). These electrodes, may be selectively interconnected with the pulse steering circuitry of FIG. 2 in the same fashion as discussed in conjunction with FIG. 6.

Figure 10:
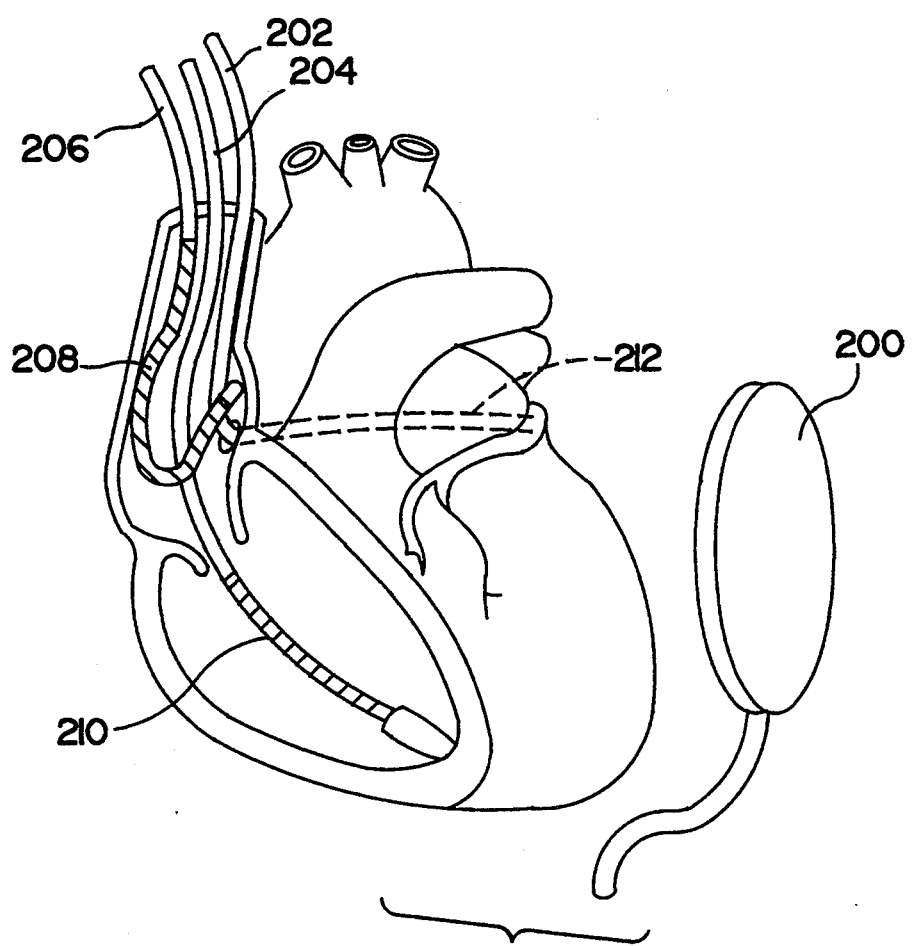
FIG. 10 is a cutaway view of the human heart illustrating the location of three transvenous and one subcutaneous electrodes which may also be employed in conjunction with the circuitry of FIGS. 1 and 2.

FIG. 10 shows a cutaway view through a human heart, illustrating an electrode system comprising a subcutaneous electrode 100 (SQ), a coronary sinus electrode I 12 (CS) mounted to a defibrillation lead 102, a right ventricular electrode I 10 (RV), mount to defibrillation lead 104, and a right atrial/superior vena cava electrode 108 (RA/SVC), mounted to a a defibrillation lead 106. Selected interconnection of these four electrodes or subsets of two or three of the illustrated four electrodes to the pulse steering circuitry of FIG. 2 can provide a wide variety of multiple pulse regimens in the context of an implantable defibrillator intended for use in conjunction with a non-thoracotomy lead system.

In conjunction with the above description, a number of specific electrode types and locations are illustrated. However, the present invention is believed to be practicable in conjunction with virtually any multiple electrode defibrillation lead system. As such, the electrodes and their locations as illustrated above should be considered exemplary, but not limiting as to the potential uses of the present invention. Similarly, while the disclosure above illustrates the use of diodes for steering the individual pulses, other passive switching circuitry, for example triac circuits similar to those disclosed in U.S. Pat. No. 5,163,427, issued to Keimel et al., which are activated by the defibrillation pulse, may readily be substituted for the diodes of the present invention. As such, the specific steering circuit illustrated in FIG. 2 should be considered exemplary, rather than limiting, with regard to the scope of the present invention as claimed below.

In conjunction with the above disclosure, I claim:
1. Apparatus for cardiac defibrillation, comprising:
a first defibrillation pulse generator, having positive and negative outputs;
a second defibrillation pulse generator, having positive and negative outputs;
first, second and third electrodes;
a steering circuit coupled to said first, second and third electrodes and to said first and second pulse generators, said steering circuit comprising switching means rendered conductive by a defibrillation pulse generated by said first pulse generator for connecting said first, second and third electrodes to said positive and negative outputs of said first pulse generator to define a first set of electrode polarities and rendered conductive by a defibrillation pulse generated by said second pulse generator for connecting said first, second and third electrodes to said positive and negative outputs of said second pulse generator to define a second set of electrode polarities different from said first set of electrode polarities.

2. Apparatus for cardiac defibrillation, comprising:
a first defibrillation pulse generator, having positive and negative outputs;
a second defibrillation pulse generator, having positive and negative outputs;
first, second and third connector means for coupling to defibrillation electrodes;
a steering circuit coupled to said first, second and third output connector means and to said first and second pulse generators, said steering circuit comprising switching means rendered conductive by a defibrillation pulse generated by said first pulse generator by said first pulse generator for connecting said first, second and third output connector means to said positive and negative outputs of said first pulse generator to define a first set of polarities and rendered conductive by a defibrillation pulse generated by said second pulse generator for connecting said first, second and third output connector means to said positive and negative outputs of said second pulse generator to define a second set of polarities different from said first set of polarities.

3. Apparatus according to claim 2, further comprising first, second and third electrodes, each said electrode provided with an electrode connector means for coupling to any of said first, second or third output connector means.

4. Apparatus for cardiac defibrillation, comprising:
a first defibrillation pulse generator, having positive and negative outputs;
a second defibrillation pulse generator, having positive and negative outputs;
first, second, third and fourth electrodes;
a steering circuit coupled to said first, second, third and fourth electrodes and to said first and second pulse generators, said steering circuit comprising switching means rendered conductive by a defibrillation pulse generated by said first pulse generator for connecting said first, second, third and fourth electrodes to said positive and negative outputs of said first pulse generator to define a first set of electrode polarities and rendered conductive by a defibrillation pulse generated by said second pulse generator for connecting said first, second, third and fourth electrodes to said positive and negative outputs of said second pulse generator to define a second set of electrode polarities different from said first set of electrode polarities.

5. Apparatus for cardiac defibrillation, comprising:
a first defibrillation pulse generator, having positive and negative outputs;
a second defibrillation pulse generator, having positive and negative outputs;
first, second, third and fourth output connector means for coupling to defibrillation electrodes;
a steering circuit coupled to said first, second, third and fourth connector means and to said first and second pulse generators, said steering circuit comprising switching means rendered conductive by a defibrillation pulse generated by said first pulse generator for connecting said first, second and third connector means to said positive and negative outputs of said first pulse generator to define a first set of polarities and rendered conductive by a defibrillation pulse generated by said second pulse generator for connecting said first, second and third connectors to said positive and negative outputs of said second pulse generator to define a second set of polarities different from said first set of polarities.

6. Apparatus according to claim 5, further comprising first, second and third electrodes, each said electrode provided with an electrode connector means for coupling to any of said first, second, third or fourth output connector means.

7. Apparatus according to claim 6 further comprising a fourth electrode provided with an electrode connector means for coupling to any of said first, second, third or fourth output connector means.

8. Apparatus for cardiac defibrillation, comprising:
a first defibrillation pulse generator, having positive and negative outputs;
a second defibrillation pulse generator, having positive and negative outputs;
first and second electrodes;
a steering circuit coupled to said first and second electrodes and to said first and second pulse generators, said steering circuit comprising switching means rendered conductive by a defibrillation pulse generated by said first pulse generator for connecting said first and second electrodes to said positive and negative outputs of said first pulse generator to define a first set of electrode polarities and rendered conductive by a defibrillation pulse generated by said second pulse generator for connecting said first and second electrodes to said positive and negative outputs of said second pulse generator to define a second set of electrode polarities different from said first set of electrode polarities.

9. Apparatus for cardiac defibrillation, comprising:
a first defibrillation pulse generator, having positive and negative outputs;
a second defibrillation pulse generator, having positive and negative outputs;
first and second connector means for coupling to defibrillation electrodes;
a steering circuit coupled to said first and second output connector means and to said first and second pulse generators, said steering circuit comprising switching means rendered conductive by a defibrillation pulse generated by said first pulse generator for connecting said first and second output connector means to said positive and negative outputs of said first pulse generator to define a first set of polarities and rendered conductive by a defibrillation pulse generated by said second pulse generator for connecting said first and second output connector means to said positive and negative outputs of said second pulse generator to define a second set of polarities different from said first set of polarities.

10. Apparatus according to claim I or claim 2 or claim 4 or claim 5 or claim 8 or claim 9 wherein said switching means are unidirectionally conductive.

11. Apparatus according to claim 10 wherein said switching means comprise diodes.

* * * * *